United States Patent [19] [11] 4,137,406
Tsuchihashi et al. [45] Jan. 30, 1979

[54] CEPHALOSPORINS HAVING A SULFUR CONTAINING FUNCTIONAL GROUP IN THE 7-POSITION SIDE CHAIN

[75] Inventors: Genichi Tsuchihashi, Tama; Katsuyuki Ogura; Masao Yaso, both of Sagamihara; Masashi Kuramoto, Shizuoka; Tadashiro Fujii, Mishima; Tetsuo Watanabe, Yokohama, all of Japan

[73] Assignees: Sagami Chemical Research Center; Toyo Jozo Co., Ltd., both of Japan

[21] Appl. No.: 773,113

[22] Filed: Feb. 28, 1977

[30] Foreign Application Priority Data

Mar. 4, 1976 [JP] Japan .................................. 51-23522

[51] Int. Cl.$^2$ .................. C07D 501/56; C07D 501/46; C07D 501/34; A61K 31/545
[52] U.S. Cl. ....................................... 544/27; 544/28; 544/25; 424/246
[58] Field of Search ......................................... 544/27

[56] References Cited
U.S. PATENT DOCUMENTS

| | | | |
|---|---|---|---|
| 3,897,422 | 7/1975 | Breuer et al. | 544/27 X |
| 3,926,983 | 12/1975 | Treuner et al. | 544/27 X |
| 4,003,893 | 1/1977 | Breuer et al. | 544/27 X |

FOREIGN PATENT DOCUMENTS 2447194 4/1975 Fed. Rep. of Germany.

Primary Examiner—Alton D. Rollins
Assistant Examiner—Diana G. Rivers
Attorney, Agent, or Firm—Wenderoth, Lind & Ponack

[57] ABSTRACT

Cephalosporins having a sulfur-containing functional group of the formula

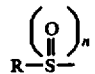

present at the carbon atom directly bonded to the thienyl or furyl group in the side chain of the 7-position of cephem derivatives. These compounds are useful as anti-bacterial agents against Gram-positive and Gram-negative bacteria.

2 Claims, No Drawings

CEPHALOSPORINS HAVING A SULFUR CONTAINING FUNCTIONAL GROUP IN THE 7-POSITION SIDE CHAIN

This invention relates to novel cephalosporins which are compounds of the general formula

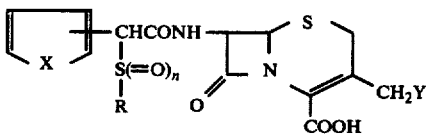

wherein R is a lower alkyl group, X is an oxygen or sulfur atom, Y is an acetoxy group, a thiadiazolylthio group substituted or unsubstituted by a lower alkyl group, a tetrazolylthio group substituted or unsubstituted by a lower alkyl group, or a pyridinium group, and n is an integer of 0 to 2;
or salts thereof.

The lower alkyl group means an alkyl group containing 1 to 5 carbon atoms. R is preferably a methyl or ethyl group in view of the ease of production and availability of starting materials. Since the compounds of formula (I) have an asymmetric carbon in the side chain at the 7-position, the cephalosporins of the present invention involve R-, S-, and RS-forms.

The salts of the above compounds are preferably those which are pharmaceutically acceptable. Examples of such salts include metal salts such as sodium, potassium, magnesium, calcium and aluminum salts, ammonium salts, and non-toxic ammonium salts thereof with di(lower)alkylamines, tri(lower)alkylamines, procaine, dibenzylamine, N,N'-dibenzylethylenediamine, N-benzyl-β-phenylethylamine, N-methylmorpholine, N-ethylmorpholine, 1-ephenamine, dehydroabietylamine, N,N'-bis-dehydroabietylethylenediamine, N-(lower)alkylpiperidines, and other amines which have heretofore been used to form salts with cephalosporins.

The compounds of the present invention are especially characteristic in that a sulfur-containing functional group of the formula

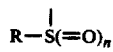

is present at the carbon atom directly bonded to the thienyl or furyl group of the formula

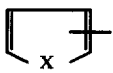

in the side chain of the 7-position of cephem derivatives.

The compounds of formula (I) and pharmaceutically acceptable salts thereof are useful as antibacterial agents because they have a superior antibacterial activity against Gram-positive and Gram-negative bacteria, especially *Sarcina lutea, Escherichia coli, Proteus vulgaris, Serratia marcescens,* and *Enterobacter aerogenes.*

The novel cephalosporins are obtained by acylating 7-aminocephem derivatives of the general formula

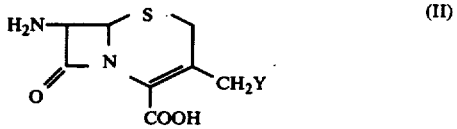

wherein Y is the same as defined hereinabove, with carboxylic acids of the general formula

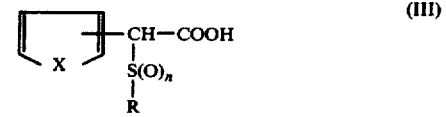

wherein R, X and n are as defined hereinabove, or reactive derivatives thereof.

Compounds of formula (I) wherein Y is other than an acetoxy group are also obtained by acylating 7-aminocephalosporanic acid (7-ACA) with the carboxylic acids (III) or reactive derivatives thereof, and reacting the resulting compounds of the general formula

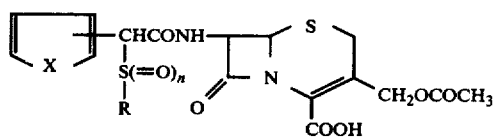

wherein R, X and n are as defined hereinabove, [i.e., compounds of formula (I) in which Y is acetoxy] with pyridine or the corresponding heterocyclethiol.

The 7-aminocephem derivatives (II) can be produced by various known methods. For example, compounds of formula (II) wherein Y is acetoxy (i.e., 7-ACA) are produced by deacylating cephalosporin C (Ce-C) or derivatives thereof chemically or biochemically. Compounds of formula (II) wherein Y is a thiadiazolylthio group optionally substituted by a lower alkyl group, a tetrazolylthio group optionally substituted by a lower alkyl group, or a pyridinium group are usually produced from 7-ACA, or by converting the acetoxy group of the 3-acetoxymethyl group of Ce-C or its derivative to the corresponding heterocyclethio group or a pyridinium group, and then chemically or biochemically deacylating the resulting compound.

The thiadiazolylthio and tetrazolylthio groups may be substituted at their heterocyclic group by a lower alkyl group such as methyl. Examples of the thiadiazolyl group are 1,2,4-thiadiazolyl groups such as 1,2,4-thiadiazol-5-yl or 3-methyl-1,2,4-thiadiazol-5-yl, and 1,3,4-thiadiazolyl groups such as 1,3,4-thiadiazol-2-yl or 5-methyl-1,3,4-thiadiazol-2-yl. The tetrazolyl group includes, for example, tetrazol-5-yl and 1-methyl-tetrazol-5-yl.

The 7-aminocephem compounds (II) are normally used as a free acid, but the carboxyl group at the 4-position may be protected by a protective group capable of being easily split off without destroying the cephalosporin skeleton. Known protective groups for carboxyl, especially those used in the production of cephalosporin compounds, can be used in the present invention. Examples of such protective groups are 2,2,2-trichloroethyl, t-butyl, benzyl, p-nitrobenzyl, p-methoxybenzyl, phenacyl, diphenylmethyl, organic silyl groups such as trimethylsilyl, organic stannyl groups such as trimethyl stannyl, and organic phosphino groups such as ethylenephosphino. The amino group at the 7-position is normally used in a free form or as a water-soluble salt. It may be activated with an organic silyl group such as trimethylsilyl, or an organic phosphino group such as ethylenephosphino.

The carboxylic acid (III), either as such or as its reactive derivatives, is used as an acylating agent for the 7-aminocephem compounds (II). These reactive derivatives denote carboxylic acid derivatives used to form amide linkages in the fields of peptide chemistry, penicillin chemistry, and cephalosporin chemistry. Examples of these derivatives are acid halides such as acid chlorides or bromides, acid azides, acid anhydrides, mixed anhydrides of acids such as arylsulfonic acids, monoesters of carbonic acid, alkylphosphoric acids, or aliphatic carboxylic acids, active esters such as p-nitrophenyl esters, p-nitrophenylthio esters, cyanomethyl esters or N-hydroxysuccinimide esters, and acid amides whose amide nitrogen is a member of a quasi-aromatic five-membered ring such as imidazole, pyrazole, triazole or tetrazole. Other acylating agents known in the art can also be used. These acylating agents and their production are described in the literature. When the carboxylic acids (III) are directly used for acylation, there may be used a dehydrolytic condensation reagent such as N,N'-diisopropylcarbodiimide, N,N'-dicyclohexylcarbodiimide, N,N'-bis(p-dimethylaminophenyl)carbodiimide, N-cyclohexyl-N'-[2-(morpholinyl-4)ethyl]carbodiimide, N-ethyl-N'-(dimethylaminopropyl)carbodiimide, N,N'-carbonylbisimidazole, phosphoryl chloride, or iso-oxazolium salts.

Carboxylic acids of formula (III) wherein X is a sulfur atom can be obtained by reacting a 1-alkylsulfinyl-1-alkylthio-2-thienylethylene with an acid chloride to form a 1,1-bis(alkylthio)-2-chloro-2-thienylethylene, reacting it with an alcohol to prepare the corresponding α-alkylthio(thienyl)acetic acid alkyl ester, hydrolyzing the ester to form a free carboxylic acid of formula (III) in which n is 0, and oxidizing the product to form the corresponding sulfinyl (n=1) or sulfonyl (n=2) compound. Carboxylic acids of formula (III) wherein X is an oxygen atom can be prepared in the same way starting from the corresponding furyl compounds.

The acylation reaction in the present invention is carried out in an inert organic solvent or in a mixture of an inert organic solvent and water. Examples of suitable inert organic solvents are acetone, tetrahydrofuran, dioxane, dimethylformamide, dimethylacetamide, dichloromethane, chloroform, dimethyl sulfoxide, methyl isobutyl ketone, and benzene. The selection of a reaction solvent depends primarily upon the form in which the 7-aminocephem derivative (II) is used. Where the 7-aminocephem derivative (II) is used in the form of a free acid or its water-soluble salt, water-containing solvents are used. When it is used in a water-insoluble form or when it is not desirable to use acylating agents in water-containing solvents, water-free solvents are employed.

The acylation reaction can be carried out at a temperature of about −50° C. to 50° C., but usually, temperatures of about −10° C. to about 15° C. are used. Where an acid is likely to be formed as a by-product in the acylation reaction, it is desirable to perform it in the co-presence of an acid acceptor, for example, an inorganic base such as an alkali bicarbonate of an alkali carbonate, or a tertiary organic base such as triethylamine, pyridine, picoline, quinoline, isoquinoline, N-methylmorpholine, N-methylpiperazine, or dimethylaniline.

The reaction product as obtained by the acylation reaction can be separated by a customary method such as concentration, solvent extraction, or chromatography, and if desired, purified by, for example, recrystallization. For example, the final desired product (I) in free form can be obtained by distilling off the organic solvent from the reaction mixture, extracting the residue after acidification with an organic solvent such as ethyl acetate, butyl acetate, methyl isobutyl ketone, chloroform or dichloromethane, washing the extract with an aqueous solution, drying it, and distilling off the solvent. The final product (I) can be obtained in the form of an alkali metal salt by adding a suitable alkali metal compound such as an alkali metal salt (e.g., a sodium salt) of hexanoic acid of 2-ethylhexanoic acid, and collecting the precipitate formed. The novel cephalosporin compound (I) or its alkali metal salt can be converted to other salts, such as other metal salts or organic amine salts, in a customary manner.

Compounds of formula (I) in which Y is a pyridinium group can be obtained by treating compounds of formula (I) in which Y is an acetoxy group with pyridine. Compounds of formula (I) in which Y is a thiadiazolylthio group or tetrazolylthio group are obtained by reacting heterocyclethiols or alkali metal salts thereof with the compound of formula (I, Y=AcO) in aqueous solution in the presence of a base such as an alkali hydrogen carbonate at a temperature of about 50 to 100° C.

The following examples specifically illustrate the production of the compounds of formula (I).

In these examples, the following carrier and solvent systems were used in thin-layer chromatography (TLC).

Carrier: a silica gel plate (20 cm; a product of Merck & Co.)

Solvent systems:
I: benzene/dioxane/acetic acid/n-butanol (90/25/4/4)
II: benzene/dioxane/acetic acid/n-butanol (60/25/12/4)

EXAMPLE 1

7-[α-Methylthio(2-thienyl)acetamido]-3-acetoxymethyl-3-cephem-4-carboxylic acid

One millimole of α-methylthio(2-thienyl)acetic acid was dissolved in 10 ml of dry tetrahydrofuran, and 1.1 millimoles of triethylamine and 1.1 millimoles of pivaroyl chloride were added to the solution at −15° C. The mixture was stirred for 1 hour, and cooled to −40° C. with dry iceacetone. A solution (obtained by stirring 1 millimole of 7-ACA and 2 millimoles of hexamethyldisilazane in 5 ml of acetonitrile for 30 minutes at 10° C.) was added to the cooled solution. The reaction was carried out at −40 to −30° C. for 90 minutes, and at room temperature for 90 minutes. The reaction mixture was concentrated under reduced pressure, and ethyl acetate was added to the residue. The mixture was washed with 1N hydrochloric acid and then with s saturated aqueous solution of sodium chloride. The ethyl acetate layer was dried over anhydrous sodium sulfate, and concentrated under reduced pressure. Solidification of the residue with petroleum ether afforded the final product.

TLC: Rf (II)=0.50

MIC (minimum inhibitory concentration) against *Sarcina lutea* (ATCC 9341): ≦ 0.2 mcg/ml IR (nujol) cm$^{-1}$: 3250, 1760, 1730, 1640, 1595, 1525, 1220, 1030, 720.

The α-methylthio(2-thienyl)acetic acid used had been prepared in the following manner.

1-Methylsulfinyl-1-methylthio-2-(2-thienyl)ethylene (5.052 g) was dissolved in 25 ml of methylene chloride, and 4 ml of triethylamine was added. Then, under cooling at −10° C., 2 ml of thionyl chloride and 25 ml of methylene chloride were added dropwise together. The mixture was stirred at −10° C. for 35 minutes, and 100 ml of methylene chloride and 30 ml of water were added. The organic layer was separated, and the aqueous layer was extracted twice with 50 ml of methylene chloride. These organic layers were combined, dried over anhydrous potassium carbonate, and concentrated under reduced pressure. The residue was chromatographed on a silica gel column using benzene as an eluant. The eluates were collected, and distilled under reduced pressure to obtain 3.869 g of a fraction having a boiling point of 113 to 124° C./0.063 to 0.1 mmHg. This fraction was dissolved in 50 ml of methanol, and 0.5 ml of methanol saturated with hydrogen chloride was added. The mixture was heated under reflux for 8 hours. After concentration under reduced pressure, the residue was distilled under reduced pressure to afford 2.322 g of methyl α-methylthio(2-thienyl)acetate as a pale yellow oil.

Boiling point: 97 – 100° C./0.08 mmHg

IR (neat): 1740, 1433, 1313, 1243, 1150, 703 cm$^{-1}$

NMR (CDCl$_3$)δ : 2.13 s (3H), 3.80 s (3H), 4.80 s (1H), 6.8-7.35 m (3H)

Elemental analysis for C$_8$H$_{10}$O$_2$S$_2$:

|  | C% | H% | S% |
|---|---|---|---|
| Calculated: | 47.50 | 4.98 | 31.70 |
| Found: | 47.84 | 5.10 | 31.33 |

Methyl α-methylthio(2-thienyl)acetate (1.956 g) was dissolved in 20 ml of 1,2-dimethoxyethane, and 10 ml of a 2N aqueous solution of potassium hydroxide was added. The mixture was stirred at room temperature for 2 hours and 50 minutes. Water (20 ml) and 10 ml of 3N sulfuric acid were added. The mixture was extracted four times with 50 ml of diethyl ether. The ethereal layer was dried over anhydrous sodium sulfate, and concentrated under reduced pressure to afford 1.668 g of α-methyl(2-thienyl)acetic acid as pale yellow crystals. Recrystallization from diethyl ether/n-hexane afforded crystals having a melting point of 75 to 75.5° C.

IR (neat): 3200–2300, 1700 cm$^{-1}$

NMR (CDCl$_3$)δ : 2.15 s (3H), 4.76 s (1H), 6.86–7.32 m (3H), 9.59 broad s (1H)

Elemental analysis for C$_7$H$_8$O$_2$S$_2$:

|  | C% | H% | S% |
|---|---|---|---|
| Calculated: | 44.66 | 4.28 | 34.06 |
| Found: | 44.53 | 4.22 | 34.05 |

EXAMPLE 2

7-[α-Methylsulfonyl(2-thienyl)acetamido]-3-acetoxymethyl-3-cephem-4-carboxylic acid Example 1 was repeated except that α-methylsulfonyl (2-thienyl)acetic acid was used instead of the α-methylthio (2-thienyl)acetic acid, thereby to obtain the above product.

TLC: Rf(II)=0.41

MIC against *Sarcina lutea* ATCC 9341: ≦ 0.2 mcg/ml

IR (KBr) cm$^{-1}$: 3400, 3020, 2950, 1760, 1675, 1610, 1370, 1310, 1260, 1230, 1140, 1120, 1030, 960, 720

The α-methylsulfonyl(2-thienyl)acetic acid used had been prepared in the following manner.

α-Methylthio(2-thienyl)acetic acid (1.731 g) was dissolved in 20 ml of methanol, and 10 mg of sodium tungstate and 3.34 ml of a 30% aqueous solution of hydrogen peroxide were added. The mixture was stirred at room temperature for 70 hours. To the reaction mixture were added 30 ml of water and 30 ml of methylene chloride. The organic layer was separated. The aqueous layer was extracted four times with 30 ml of methylene chloride. The resulting organic layers were combined, dried over anhydrous sodium sulfate, and concentrated under reduced pressure to afford yellow crystals. The crystals were dissolved in benzene, and the insoluble matter was separated by filtration. The residue was concentrated under reduced pressure. Recrystallization of the resulting yellow crystals from benzene/n-hexane afforded 997 mg of α-methylsulfonyl(2-thienyl)acetic acid as pale yellow crystals.

EXAMPLE 3

7-[α-Methylthio(3-thienyl)acetamido]-3-acetoxymethyl-3-cephem-4-carboxylic acid

Example 1 was repeated except that α-methylthio (3-thienyl)acetic acid was used instead of α-methylthio(2-thienyl)acetic acid, thereby to obtain the above product.

TLC: Rf(II)=0.56

IR (KBr) cm$^{-1}$: 3350, 2960, 1775, 1730, 1660, 1630, 1515, 1380, 1230, 1030.

The α-methylthio(3-thienyl)acetic acid used had been prepared in the following manner.

1,1-Bis(methylthio)-2-chloro-2-(3-thienyl) ethylene (10.886 g) was dissolved in 100 ml of methanol, and 1 ml of methanol saturated with hydrogen chloride was added. The mixture was heated under reflux for 16 hours and 40 minutes. The reaction mixture was concentrated under reduced pressure, and the residue was distilled under reduced pressure to afford 7.178 g of a fraction of methyl α-methylthio(3-thienyl)acetate having a boiling point of 80 to 95° C. (mainly 93 to 95° C.)/0.12 mmHg. Samples for analysis were obtained by re-distillation.

IR (neat): 1738 cm$^{-1}$

NMR (CDCl$_3$)δ: 2.04 s (3H), 3.72 s (3H), 4.56 s (1H), 7.05–7.40 m (3H).

Elemental analysis for C$_8$H$_{10}$O$_2$S$_2$:

|  | C% | H% | S% |
|---|---|---|---|
| Calculated: | 47.50 | 4.98 | 31.70 |
| Found: | 47.60 | 4.95 | 31.46 |

Methyl α-methylthio(3-thienyl)acetate (5.045 g) was dissolved in 60 ml of 1,2-dimethoxyethane, and 20 ml of a 2N aqueous solution of potassium hydroxide was added. The mixture was stirred at room temperature for 3 hours and 10 minutes. To the reaction mixture were added 30 ml of water and 6 ml of 3N sulfuric acid. The mixture was extracted three times with 50 ml of diethyl ether. The ethereal layer was dried over anhydrous sodium sulfate, and concentrated under reduced pressure. Recrystallization of the residue from benzene/n-hexane afforded 3.291 g of α-methylthio(3-thienyl)acetic acid as pale yellow crystals having a melting point of 73.5 to 74.0° C.

EXAMPLE 4

7-[α-Methylsulfonyl(3-thienyl)acetamido]-3-acetoxymethyl-3-cephem-4-carboxylic acid Example 1 was repeated except that α-methylsulfonyl(3-thienyl)acetic acid was used instead of α-methyl(2-thienyl)acetic acid, thereby to afford the above product.

TLC: Rf(I)=0.51

MIC against *Sarcina lutea* ATCC 9341: ≦ 0.2 mcg/ml

IR (KBr) cm$^{-1}$: 3360, 2950, 1778, 1730, 1680, 1520, 1380, 1310, 1230, 1030, 965

The α-methylsulfonyl(3-thienyl)acetic acid used had been prepared in the following manner.

α-Methylthio(3-thienyl)acetic acid (1.487 g) was dissolved in 20 ml of methanol, and 10 mg of sodium tungstate and 2.5 ml of a 30% aqueous solution of hydrogen peroxide were added. The mixture was stirred for 3 days. To the reaction mixture was added 50 ml of water, and the mixture was extracted four times with 80 ml of methylene chloride. The organic layer was dried over anhydrous sodium sulfate, and concentrated under reduced pressure. Crystallization of the residue from methylene chloride/carbon tetrachloride afforded 950 mg of α-methylsulfonyl(3-thienyl)acetic acid as pale yellow crystals having a melting point of 123 to 123.5° C.

EXAMPLE 5

7-[α-Methylthio(2-thienyl)acetamido]-3-(5-methyl-1,3,4-thiadiazol-2-ylthiomethyl)-3-cephem-4-carboxylic acid 7-[α-Methylthio(2-thienyl)acetamido]-3-acetoxymethyl-3-cephem-4-carboxylic acid (1.1 g), 0.4 g of 5-methyl-2-mercapto-1,3,4-thiadiazole and 0.21 g of sodium bicarbonate were added to 20 ml of a phosphate buffer (pH 6.4), and the mixture was then stirred at 60° C. for 20 hours. The reaction mixture was washed with diethyl ether. The aqueous layer was poured into 200 ml of dilute hydrochloric acid, and extracted with ethyl acetate. The ethyl acetate layer was washed with a saturated aqueous solution of sodium chloride, dried over anhydrous sodium sulfate, and concentrated under reduced pressure to afford 0.62 g of the above product.

TLC: Rf(II)=0.44

MIC against *Sarcina lutea* ATCC 9341: ≦ 0.2 mcg/ml

IR (KBr) cm$^{-1}$: 3420, 3060, 2870, 1770, 1665, 1510, 1420, 1270, 1060, 740, 710

EXAMPLE 6

7-[α-Methylthio(3-thienyl)acetamido]-3-(5-methyl-1,3,4-thiadiazol-2-ylthiomethyl)-3-cephem-4-carboxylic acid 7-[α-Methylthio(3-thienyl)acetamido]-3-acetoxymethyl-3-cephem-4-carboxylic acid (1.1 g), 0.4 g of 5-methylmercapto-1,3,4-thiadiazole and 0.21 g of sodium bicarbonate were dissolved in 20 ml of a phosphate buffer (pH 6.4), and the solution was stirred at 60° C. for 12 hours. The reaction mixture was worked up in the same way as set forth in Example 5 to afford 0.68 g of the above product.

TLC: Rf(II)=0.39

IR (KBr) cm$^{-1}$: 3375, 2975, 1775, 1730, 1650, 1510, 1370, 1220, 1060

EXAMPLE 7

N-[7-{α-methylthio(2-thienyl)acetamido}-3-cephem-3-ylmethyl]pyridinium-4-carboxylate 7-[α-Methylthio(2-thienyl)acetamido]-3-acetoxymethyl-3-cephem-4-carboxylic acid (1.0 g) was suspended in 10 ml of water, and 1 ml of pyridine was added. The mixture was stirred until the acid dissolved. The resulting solution (pH 5.9) was maintained at 35° C. for 3 days. After filtration, it was extracted four times with 10 ml of chloroform. The extract was extracted with a small amount of water, and the aqueous solution was allowed to flow through a column of an acetate-form Dowex 1 × 8 (100 to 200 mesh, 20 g). The column was washed with water, and the eluate obtained was lyophilized. The dried product obtained was treated with a small amount of methanol, filtered off and dried to afford the above final product.

Elemental analysis for $C_{20}H_{19}O_4N_3S_3$:

|  | C% | H% | N% |
|---|---|---|---|
| Calculated: | 52.04 | 4.15 | 9.10 |
| Found: | 51.86 | 4.21 | 8.97 |

EXAMPLE 8

7-[α-Methylthio(2-thienyl)acetamido]-3-(1-methyl-1H-tetrazol-5-ylthiomethyl)-3-cephem-4-carboxylic acid Example 5 was repeated except that 1-methyl-5-mercapto-1H-tetrazole (360 mg) was used instead of 5-methyl-2-mercapto-1,3,4-thiadiazole, thereby to afford the above product (1.0 g). The powder thus obtained was chromatographed on a 100 ml column of an absorbent resin HP-20 (a product of Mitsubishi Chemical Co. Ltd.) using acetone/water as an eluant to afford 240 mg of the final product.

TLC: Rf(II)=0.36

MIC against *Sarcina lutea* ATCC 9341: ≦ 0.2 mcg/ml

MIC against *Enterobacter aerogenes*: 25 mcg/ml (That of Cephalothin:> 100 mcg/ml)

Elemental analysis for $C_{17}H_{18}N_6O_4S_4$:

|  | C% | H% | N% |
|---|---|---|---|
| Calculated: | 40.95 | 3.64 | 16.85 |
| Found: | 40.67 | 3.56 | 17.08 |

EXAMPLE 9

7-[α-Methylthio(2-furyl)acetamide]-3-acetoxymethyl-3-cephem-4-carboxylic acid

Example 1 was repeated except that α-methylthio-(2-furyl)acetic acid was used instead of the α-methylthio-(2-thienyl)acetic acid, thereby to afford the above product.

TLC: Rf(II)=0.38

MIC against *Sarcina lutea* ATCC 9341: ≦ 0.2 mcg/ml

Elemental analysis values for $C_{17}H_{18}O_7N_2S_2$:

|  | C% | H% | N% |
|---|---|---|---|
| Calculated: | 47.88 | 4.25 | 6.57 |
| Found: | 48.03 | 4.12 | 6.66 |

The α-methylthio(2-furyl)acetic acid used had been prepared in the following manner.

1,1-Bis(methylthio)-2-chloro-2-(2-furyl)ethylene (5.67 g) was dissolved in 100 ml of methanol, and 1 ml of methanol saturated with hydrogen chloride was added. The mixture was heated under reflux for 15 hours and 10 minutes. The reaction mixture was concentrated under reduced pressure. The residue was chromatographed on a silica gel column using benzene/n-hexane as an eluant. The eluates were concentrated under reduced pressure to afford 3.811 g of methyl α-methylthio(2-furyl)acetate as a pale yellow oil.

IR (neat): 1744 cm$^{-1}$
NMR (CDCl$_3$)δ: 2.08 s (3H), 3.73 s (3H), 4.56 s (1H), 6.29 dxd (1H, J=2, 3Hz), 6.41 dxd (1H, J=0.5, 3Hz), 7.34 dxd (1H, J=0.5, 2Hz)

In the same way as in Example 1, this oil was hydrolyzed with potassium hydroxide in 1,2-dimethoxyethane, and the crude product obtained was crystallized from hexane/benzene to afford α-methylthio(2-furyl)acetic acid having a melting point of 62.0 to 62.5° C.

IR (KBr): 3300-2000, 1698 cm$^{-1}$
NMR (CDCl$_3$)δ: 2.12 s (3H), 4.58 s (1H), 6.29 dxd (1H, J=2, 3Hz), 6.44 dxd (1H, J=1, 3Hz), 7.35 dxd (1H, J=1, 2Hz), 9.50 broad s (1H)

Elemental analysis for C$_7$H$_8$O$_3$S:

|  | C% | H% | S% |
|---|---|---|---|
| Calculated: | 48.82 | 4.68 | 18.62 |
| Found: | 48.87 | 4.72 | 18.75 |

EXAMPLE 10

7-[α-Methylsulfonyl(2-furyl)acetamido]-3-acetoxymethyl-3-cephem-4-carboxylic acid Example 1 was repeated except that α-methylsulfonyl(2-furyl)acetic acid was used instead of α-methylthio(2-thienyl)acetic acid, thereby to afford the above product.

TLC: Rf(II)=0.25
MIC against *Sarcina lutea* ATCC 9341: 0.8 mcg/ml
Elemental analysis for C$_{17}$H$_{18}$O$_9$N$_2$S$_2$:

|  | C% | H% | N% |
|---|---|---|---|
| Calculated: | 44.57 | 3.96 | 6.11 |
| Found: | 44.88 | 4.08 | 5.90 |

The α-methylsulfonyl(2-furyl)acetic acid used had been obtained by oxidizing α-methylthio(2-furyl)acetic acid in the same way as in Example 2. Its melting point was 97 - 97.5° C.

EXAMPLE 11

7-[α-Methylthio(2-furyl)acetamido]-3-acetoxymethyl-3-cephem-4-carboxylic acid

α-Methylthio(2-furyl)acetic acid (2.00 g) was suspended in 120 ml of tetrahydrofuran, and 1.62 ml of triethylamine was added. The mixture was cooled to −10 to −12° C. To the mixture was added a solution of 1.40 g of pivaloyl chloride in 20 ml of tetrahydrofuran over the course of 10 minutes, and the mixture was stirred for 30 minutes. A solution obtained by stirring 3.80 g of 7-ACA and 1.96 ml of triethylamine in 180 ml of dichloromethane was added dropwise over the course of 35 minutes at below −10° C. The mixture was stirred for 1 hour at this temperature, for 1 hour at 0 to 3° C., and then for 1 hour at room temperature. The insoluble matter was then separated by filtration. The filtrate was acidified with 1N hydrochloric acid, and extracted with dichloromethane. The dichloromethane layer was extracted once with 80 ml, 40 ml and 20 ml of a 3% aqueous solution of sodium bicarbonate. The water layer was acidified with 1N hydrochloric acid, and extracted with 200 ml of ethyl acetate and then with 100 ml of ethyl acetate. The ethyl acetate layer was washed four times with a saturated aqueous solution of sodium chloride, dried over anhydrous sodium sulfate, and concentrated under reduced pressure. Petroleum ether was added to the oily residue, and it was powderized. By filtration, 2.8 g of a powder was obtained. The powder was chromatographed on a 1-liter column of an adsorbent resin HP-20 (a product of Mitsubishi Chemical Co. Ltd.) using acetone/water as an eluant to afford 0.85 g of the final product having one spot on a silica gel thin-layer chromatogram.

TLC: Rf(II)=0.38
MIC against *Sarcina lutea* ATCC 9341: ≦ 0.2 mcg/ml

EXAMPLE 12

7-[α-Methylthio(2-furyl)acetamido]-3-(5-methyl-1,3,4-thiadiazol-2-ylthiomethyl)-3-cephem-4-carboxylic acid 7-[α-Methylthio(2-furyl)acetamido]-3-acetoxymethyl-3-cephem-4-carboxylic acid (341 mg), 128 mg of 2-mercapto-5-methyl-1,3,4-thiadiazole and 68 mg of sodium bicarbonate were dissolved in 10 ml of a 0.1M phosphate buffer (pH 6.4), and the solution was stirred at 60° C. for 7 hours, and then at room temperature for 14 hours. Then, 10 ml of water was added, and the mixture was washed with diethyl ether. The aqueous layer was acidified with 1N hydrochloric acid to a pH of 2, and extracted three times with ethyl acetate. The ethyl acetate layer was washed with a saturated aqueous solution of sodium chloride, dried over magnesium sulfate, and then concentrated under reduced pressure. Petroleum ether was added to the residue, and it was powderized. By filtration, the final product was obtained.

TLC: Rf(II)=0.33
MIC against *Sarcina lutea* ATCC 9341: ≦ 0.2 mcg/ml

EXAMPLE 13

7-[α-Methylthio(2-furyl)acetamido]-3-(1-methyl-1H-tetrazol-5-ylthiomethyl)-3-cephem-4-carboxylic acid Example 12 was repeated except that 120 mg of 1-methyl-5-mercapto-1H-tetrazole was used instead of 128 mg of 2-mercapto-5-methyl-1,3,4-thiadiazole, thereby to obtain the above product in powder form.

TLC: Rf(II)=0.30
MIC against *Sarcina lutea* ATCC 9341: ≦ 0.2 mcg/ml
MIC against *Serratia marcescens*: 25 mcg/ml (That of Cephalothin: > 100 mcg/ml)
MIC against *Enterobacter aerogenes*: 25 mcg/ml (That of Cephalothin: > 100 mcg/ml)

EXAMPLE 14

7-[α-Methylsulfonyl(2-furlyacetamido]-3-acetoxymethyl-3-cephem-4-carboxylic acid α-Methylsulfonyl(2-furyl)acetic acid (5.72 g) was dissolved in 120 ml of tetrahydrofuran, and 3.24 ml of triethylamine was added. The mixture was stirred at below −12° C. A solution of 2.80 g of pivaloyl chloride in 20 ml of tetrahydrofuran was added dropwise over the course of 10 minutes, and the mixture was stirred at −13 to −15° C. for 30 minutes. A solution obtained by stirring 7.60 g of 7-ACA and 3.92 g of triethylamine in 120 ml of dichloromethane was added dropwise at −10 to −12° C. over the course of 30 minutes. The mixture was stirred at the same temperature for 1 hour, at 0° C. for 1 hour, and then at room temperature for 1 hour. To the reaction mixture were added 100 ml of water, 200 ml of a saturated aqueous solution of sodium bicarbonate and 200 ml of ethyl acetate for extraction. The aqueous layer was acidified with 1N hydrochloric acid to a pH of 2, and extracted once with 400 ml of ethyl acetate and then twice with 100 ml of ethyl acetate. The ethyl acetate layer was washed four times with a saturated aqueous solution of sodium chloride, dried over anhydrous magnesium sulfate, and concentrated under reduced pressure. The oily residue was powderized after addition of petroleum ether, and by filtration, the final product was obtained.

TLC: Rf(II)=0.25
MIC against *Sarcina lutea* ATCC 9341: 0.8 mcg/ml

EXAMPLE 15

7-[α-Methylsulfonyl(2-furyl)acetamido]-3-(5-methyl-1,3,4-thiadiazol-2-ylthiomethyl)-3-cephem-4-carboxylic acid 7-[α-Methylsulfonyl(2-furyl)acetamido]-3-acetoxymethyl-3-cephem-4-carboxylic acid (366.4 mg), 128 mg of 2-mercapto-5-methyl-1,3,4-thiadiazole and 68 mg of sodium bicarbonate were dissolved in a 0.1N phosphate buffer (pH 6.4), and the solution was stirred at 60° C. for 8 hours. Then, 20 ml of water, and 50 ml of ethyl acetate were added for extraction. The aqueous layer was acidified with 1H hydrochloric acid to a pH of 2, and extracted with ethyl acetate three times. The organic layer was washed four times with a saturated aqueous solution of sodium chloride, dried over magnesium sulfate, and concentrated under reduced pressure to obtain the product in powder form.

TLC: Rf(II)=0.21
MIC against *Sarcina lutea* ATCC 9341: 0.4 mcg/ml

EXAMPLE 16

7-[α-Methylsulfonyl(2-furyl)acetamido]-3-(1-methyl-1H-tetrazol-5-ylthiomethyl)-3-cephem-4-carboxylic acid Example 15 was repeated except that 120 mg of 1-methyl-5-mercapto-1H-tetrazole was used instead of 128 mg of 2-mercapto-5-methyl-1,3,4-thiadiazole, thereby to obtain the above product in powder form.

TLC: Rf(II)=0.20
MIC against *Sarcina lutea* ATCC 9341: ≦ 0.2 mcg/ml
MIC against *Serratia marcescens*: 25 mcg/ml (That of Cephalothin:> 100 mcg/ml)

EXAMPLE 17

7-[α-Methylsulfonyl(2-thienyl)acetamide]-3-(5-methyl-1,3,4-thiadiazol-2-ylthiomethyl)-3-cephem-4-carboxylic acid 7-[α-Methylsulfonyl(2-thienyl)acetamide]-3-acetoxymethyl-3-cephem-4-carboxylic acid (474 mg), 160 mg of 5-methyl-2-mercapto-1,3,4-thiadiazole and 84 mg of sodium bicarbonate were added to 10 ml of a 0.1N phosphate buffer (pH 6.4), and the mixture was stirred at 60° C. for 24 hours. Then, 10 ml of water was added, and the mixture was washed with diethyl ether. The aqueous layer was adjusted to pH 2 with 1N hydrochloric acid, and extracted three times with ethyl acetate. The ethyl acetate layer was washed with a saturated aqueous solution of sodium chloride, dried over anhydrous sodium hydrate, and concentrated under reduced pressure. The residue was treated with petroleum ether to obtain the final product. The product was dissolved in an aqueous solution of sodium bicarbonate, and chromatographed on a column of an adsorbent resin NP-20 (150 ml) using acetone/water as an eluant to afford 40 mg of a powder.

TLC: Rf(II)=0.30
MIC against *Sarcina lutea* ATCC 9341: ≦ 0.2 mcg/ml
MIC against *Enterobacter aerogenes*: 25 mcg/ml (That of Cephalothin: > 100 mcg/ml)

EXAMPLE 18

7-[α-Methylsulfonyl(2-thienyl)acetamide]-3-(1-methyl-1H-tetrazol-5-ylthiomethyl)-3-cephem-4-carboxylic acid Example 17 was repeated except that 144 mg of 1-methyl-5-mercapto-1H-tetrazole was used instead of the 5-methyl-2-mercapto-1,3,4-thiadiazole. The resulting final product was dissolved in an aqueous solution of sodium bicarbonate, and chromatographed on a column of an adsorbent resin HP-20 (40 ml) using acetone/water as an eluant to afford 57.3 mg of a powder.

TLC: Rf(II)=0.27
MIC against *Sarcina lutea* ATCC 9341: ≦ 0.2 mcg/ml
MIC against *Serratia marcescens*: 6.3 mcg/ml (That of Cephalothin: > 100 mcg/ml)
MIC against *Enterobacter aerogenes*: 6.3 mcg/ml (That of Cephalothin: > 100 mcg/ml)

What we claim is:

1. A compound of the formula:

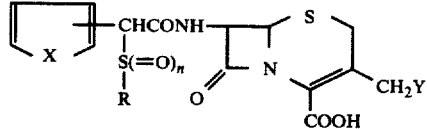

wherein R equals methyl, X equals O or S, Y equals 1-methyl-1-H-tetrazol-5-ylthio and n equals 0 to 2.

2. The compound of the formula:

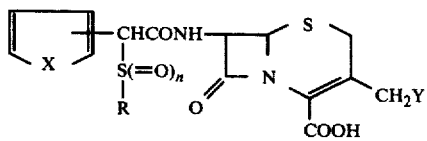

wherein R equals methyl, X equals S, Y equals 1-methyl-1-H-tetrazol-5-ylthio and n equals 0 or 2.

* * * * *